United States Patent

Miura et al.

Patent Number: 5,653,957
Date of Patent: Aug. 5, 1997

[54] HALOGENATED SULFIDOHYDROBORANES FOR NUCLEAR MEDICINE AND BORON NEUTRON CAPTURE THERAPY

[75] Inventors: Michiko Miura, Hampton Bays; Daniel N. Slatkin, Southold, both of N.Y.

[73] Assignee: Associated Universities, Inc., Washington, D.C.

[21] Appl. No.: 740,693

[22] Filed: Nov. 1, 1996

Related U.S. Application Data

[62] Division of Ser. No. 427,673, Apr. 24, 1995, which is a division of Ser. No. 118,300, Sep. 9, 1993, Pat. No. 5,455,022.

[51] Int. Cl.$^6$ .................................................. A61K 51/00
[52] U.S. Cl. ............................................................. 424/1.61
[58] Field of Search .................................................. 424/1.61

[56] References Cited

U.S. PATENT DOCUMENTS

| | | | |
|---|---|---|---|
| 5,256,394 | 10/1993 | Spielvogel | 424/5 |
| 5,455,022 | 10/1995 | Miura et al. | 424/1.61 |
| 5,489,673 | 2/1996 | Wilbur | 536/17.1 |

OTHER PUBLICATIONS

Knoth et al., "Chemistry of Boranes" *Inorg. Chem.*, 3(2), pp. 159–167 1964.
Knoth et al., "Chemistry of Boranes", *J. Am. Chem. Soc.*, 86, pp. 3972–3983 1964.

*Primary Examiner*—John Kight
*Assistant Examiner*—Lara C. Kelley
*Attorney, Agent, or Firm*—M. C. Bogosian

[57] ABSTRACT

A method for performing boron neutron capture therapy for the treatment of tumors is disclosed. The method includes administering to a patient an iodinated sulfidohydroborane, a boron-10-containing compound. The site of the tumor is localized by visualizing the increased concentration of the iodine labelled compound at the tumor. The targeted tumor is then irradiated with a beam of neutrons having an energy distribution effective for neutron capture. Destruction of the tumor occurs due to high LET particle irradiation of the tissue secondary to the incident neutrons being captured by the boron-10 nuclei. Iodinated sulfidohydroboranes are disclosed which are especially suitable for the method of the invention. In a preferred embodiment, a compound having the formula $Na_4B_{12}I_{11}SSB_{12}I_{11}$, or another pharmaceutically acceptable salt of the compound, may be administered to a cancer patient for boron neutron capture therapy.

17 Claims, 1 Drawing Sheet

$B_{24}I_{22}S_2$    ○ = BI    ◍ = B

HALOGENATED SULFIDOHYDROBORANES FOR NUCLEAR MEDICINE AND BORON NEUTRON CAPTURE THERAPY

This application is a divisional of co-pending application Ser. No. 08/427,673 filed Apr. 24, 1995, which in turn is a divisional of application Ser. No. 08/118,300 filed Sep. 9, 1993, and now U.S. Pat. No. 5,455,022 issued Oct. 3, 1995.

This invention was made with U.S. Government support under Department of Energy Contract Number DE AC02-76CH00016 and under National Institutes of Health Grant Number IR01CA38107-01A2. The U.S. Government has certain rights in the invention.

BACKGROUND OF THE INVENTION

1. Field of the Invention

The present invention relates to boron-containing compounds useful in boron neutron capture therapy of tumors and to methods for using such compounds. The compounds of the present invention provide a means for directly quantifying boron concentrations in tissue, thereby permitting rapid enhanced targeting and planning of neutron-capture irradiation of tumors.

2. Background of the Related Art

Cancer continues to be one of the foremost health problems. Conventional treatments such as surgery, photon radiation therapy, and chemotherapy have been successful in certain cases and unsuccessful in others. An unfamiliar form of radiation therapy for cancer, known as Boron Neutron-Capture Therapy (BNCT), is being investigated to treat certain tumors for which the conventional methods have been ineffective. For example, BNCT has been used clinically in Japan to treat glioblastoma multiforme, a highly malignant, invasive form of brain cancer.

BNCT is an anti-cancer bimodal radiation therapy that utilizes the ability of the stable (non-radioactive) nucleus boron-10 ($^{10}B$) to absorb thermal neutrons. In BNCT of malignant brain tumors, the patient is first given an infusion of a boron-containing compound that is highly enriched in the $^{10}B$ isotope. Ideally, the boronated compound concentrates preferentially in the brain tumor. For some boron compounds under investigation in BNCT research, the action of the blood-brain-barrier generally minimizes their entry into the surrounding brain tissues. The tumor area is then irradiated with a beam of thermal neutrons (primary irradiation), some of which are captured by the boron-10 concentrated in the tumor. The relative probability that the slow-moving thermal neutrons will be absorbed by the boron-10 nuclide is high compared to the probability of absorption by most all other nuclides in the issue combined, i.e., the nuclides normally present in mammalian tissues. Boron-10 undergoes the following nuclear reaction when captured by a thermal neutron:

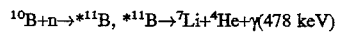

$$^{10}B+n \rightarrow *^{11}B,\ *^{11}B \rightarrow {}^{7}Li+{}^{4}He+\gamma(478\ keV)$$

In this nuclear reaction, a $^{10}B$ nucleus absorbs a neutron, forming the metastable nuclide $*^{11}B$, which spontaneously disintegrates into a $^{4}He$ particle and a $^{7}Li$ particle, bearing a total kinetic energy of 2.34 MeV. These two particles have 9 μm and 5 μm ranges in tissue, respectively. Accordingly, the particles are capable of destroying cells such as cancer cells, and/or cells of the blood vessels in the tumor that allow the cancer to grow, the nuclei of which are in their trajectories. In effect, the tumor alone is preferentially irradiated with these high linear energy transfer (LET) alpha and $^{7}Li$ particles whose range in tissue is about 10 μm, a distance comparable to the diameter of an average cell. Therefore, the efficacy of BNCT resides in the production of highly localized, ionizing radiation in the target tissue. In this manner, the tumor receives a relatively large radiation dose, compared to that received by the surrounding healthy tissue. Optimally, the preferential accumulation of boron the tumor permits the radiation dose to the tumor to exceed the dose to the blood vessels of the surrounding normal brain and to greatly exceed the dose to the extravascular normal brain tissue.

Several criteria must be met in order for radiation enhancement provided by BNCT to be successful. First, the $^{10}B$ must be present in significant quantities at the tumor site (at least about 10 mg, and preferably more than about 30 mg $^{10}B$/g tissue). Second, there should be high selectivity of the drug for the tumor over normal tissue, with tumor-to-normal tissue ratios greater than two. Generally, this second criterion is satisfied if the boronated drug does not penetrate the blood brain barrier. Third, the tumor-to-blood ratio should be not less than one. Fourth, the boronated drug should not be significantly toxic to the patients being treated. However, considering the seriousness of malignant brain tumors, moderately toxic chemotherapeutic agents and other therapeutic agents are widely used.

BNCT differs from other cancer therapy modalities. For example, BNCT differs from conventional radiotherapy modalities because it uses an external beam to produce a high radiation dose only where a chemical compound has accumulated prior to irradiation. BNCT also differs from chemotherapy because the compound that accumulates in the tumor expresses its tumoricidal action only within the field of the neutron radiation beam. The efficacy of BNCT therefore depends not only upon the relative concentrations of boron in the blood, in the tumor and in other vital tissues within the treatment volume, but also depends the quality of the neutron beam.

The concentrations of $^{10}B$ within the tissues of patients have been estimated indirectly by pharmacokinetic extrapolation from the concentration of $^{10}B$ in blood and tissue samples from patients and from experimental animals. Such extrapolations are approximate. It would therefore be desirable to have a method for more directly, more rapidly, and more accurately determining the concentration and distribution of $^{10}B$ in a patient being prepared for BNCT. The implementation of rapid BNCT treatment planning, enabled by relatively common and cost effective imaging techniques such as computerized tomography (CT) and nuclear medicine scintigraphy, would greatly facilitate the clinical acceptance and efficacy of BNCT.

The simultaneous labeling of antibodies with $^{10}B$ and with other nuclides, including iodine, for purposes of imaging tumors and targeting thermal neutron radiation exposures are described in U.S. Pat. Nos. 4,348,376 to Goldenberg, 4,665,897 to Lemelson, and 4,824,659 to Hawthorne. Each of these patents, however, requires that the $^{10}B$ compound be linked to a radio-labeled antibody. None of these patents discloses boron compounds that are targeted nonspecifically, nor do they disclose nonradioactive iodination of boron-containing compounds for imaging. In addition, the iodine is described in these patents as being directly substituted for hydrogen atoms on the antibody molecule, but not into the borane moiety.

Specifically, U.S. Pat. No. 4,348,376 to Goldenberg describes methods for radiolabeling antibodies to carcinoembryonic antigen (CEA), a cell surface marker commonly associated with certain types of tumors. The anti-CEA antibodies are described as being coupled to a $^{10}B$-containing moiety including, for example, the diazonium ion derived from 1-(4-aminophenyl)-1,2-dicarbacloso-dodecaborane. Goldenberg further describes methods for radiolabeling the boron rich antibody complex using any of a group of radioisotopes that emit detectable particle or photon radiation, for example, iodine-131 ($^{131}I$), iodine-123 ($^{123}I$), or iodine-125 ($^{125}I$).

U.S. Pat. No. 4,665,897 to Lemelson discloses a method of radiolabeling antibodies, desirably antibodies specific for tumors. Lemelson describes a variety of boron-containing moieties that may be coupled to the antibodies. Lemelson also describes the additional coupling of radionuclides, including isotopes of iodine, to the antibody moiety of the boron-coupled antibodies. The isotopes used for imaging of the target tissues are described by Lemelson as either stable or radioactive, allowing for targeting by imaging of either stimulated or spontaneous emission of radiation. Lemelson does not describe boranes as added moieties or the iodination of boranes, nor does Lemelson describe a method for adding sufficient stable iodine to antibodies in amounts that would allow chemical noninvasive imaging while also allowing the antibodies to retain their antigenic specificity for a tumor.

U.S. Pat, No. 4,824,659 to Hawthorne describes the modification of antibodies by coupling them to a synthetic poly(amide/urea/thiourea) moiety containing any of various boranes, resulting in antibody conjugates carrying 50–2000 boron atoms with about 96% $^{10}B$ content. The Hawthorne patent describes a variety of other antibody conjugates, including antineoplastic agents, paramagnetic spin labels, chromogens, etc., in addition to $^{10}B$ borane compounds. Hawthorne also describes the coupling of radionuclides, including isotopes of iodine, to the antibody moiety of the borane-antibody complex, for in vivo diagnostic use.

The use of radioisotope-labeled therapeutic substances for purposes of PET imaging of blood concentration and feedback control of the rate of administration of the labeled substances is described in U.S. Pat. No. 4,409,966 to Lambrecht et al. The Lambrecht et al. patent, however, does not disclose compounds containing boron for BNCT. Lambrecht et al. also describe the application of their method to the injection of other radiopharmaceuticals. Unlike the present invention, Lambrecht et al. employ a pharmaceutical labeled with a positron-emitting isotope for detection by Positron Emission Tomograph (PET). Lambrecht et al. do not describe the use of $^{10}B$ carriers as an aspect of their method. Nor do they describe the use of the technique for imaging drug concentrations around tumors or for the targeting of radiation therapy.

Thiouracil derivatives of decaboranes used for BNCT are described in U.S. Pat. Nos. 5,116,980 and 5,144,026 to Gabel. These patents disclose a variety of compounds and their intermediates that may be used for BNCT, but do not describe labeling of the compounds for imaging purposes. They disclose halogenated boranes such as omega-carboranyl acyl halides. Gabel does not describe the use of these compounds as therapeutic agents. Rather, the compounds are described as intermediates in the actions required to produce the therapeutic thiouracil derivatives. Further, Gabel does not disclose imaging of blood concentrations of $^{10}B$ carriers. The Gabel patents do not describe the use of nuclide-labeled $^{10}B$ carriers for simultaneous imaging and therapeutic use in BNCT.

A review of the history of BNCT as applied to brain tumors is provided in a publication by one of the co-inventors, Slatkin, "A History of Boron Neutron Capture Therapy of Brain Tumours", Brain, 114 1609–1629 (1991). This article describes uses of $^{10}B$ carriers before 1991, such as sulfidohydroboranes, including $Na_2B_{12}H_{11}SH$ (a monomer hereinafter abbreviated BSH) and $Na_4B_{24}H_{22}S_2$ (a dimer hereinafter abbreviated BSSB). Slatkin mentions the need for techniques capable of generating data on the distribution of BNCT agents in patients, but does not describe any means for noninvasive imaging of $^{10}B$-carriers. Slatkin also mentions the use of BSH and BSSB in clinical studies in Japan. See also Joel et al., "Boron Neutron Capture Therapy of Intracerebral Rat Gliosarcomas", Proc. Natl. Acad. Sci. USA, 87, 9808 (1990). See also U.S. Statutory Invention Registration No. H505to Slatkin et al.

Chemical methods for halogenating, for example iodinating, decaboranes and dodecaboranes are described by Knoth et al., "Chemistry of Boranes. IX. Halogenation of $B_{10}H_{10}^{-2}$ and $B_{12}H_{12}^{-2}$", Inorg. Chem., 3(2), 159–167 (1964). The article is limited to the particular synthetic methods described, and does not describe or suggest any application of iodinated boranes to BNCT. Unlike the present invention which describes the use of sulfidohydroboranes, Knoth et al., do not describe or suggest sulfur-containing boranes in that particular article, although Knoth is the principal author of the first publication that described the synthesis of BSH, see Knoth et al., "Chemistry of Boranes. XIX. Derivative Chemistry of $B_{10}H_{10}^{-2}$ and $B_{12}H_{12}^{-2}$", J. Am. Chem. Soc., 86, 3973–3983 (1964).

Therefore, it would be advantageous to improve prospects for clinical BNCT that facilitates the selective uptake by tumors of a non-specific halogenated $^{10}B$-carrier and the simultaneous visualization of iodine-labeled $^{10}B$ concentrations within a patient for purposes of targeting a therapeutic neutron beam.

Accordingly, it is a purpose of the present invention to provide iodinated, boron-containing compounds that are useful in BNCT and that simultaneously enable visualization of the compound for purposes of rapidly and directly targeting the tumor and estimating the neutron irradiation dose.

It is also a goal of the present invention to provide an improved method of BNCT in which an iodinated boron compound serves as the therapeutic agent and, at the same time, enables the targeting of a neutron beam.

It is a further purpose of the present invention to provide methods for the synthesis of iodinated sulfidohydroborane compounds useful for BNCT and visualization of the boron biodistribution of these compounds in vivo.

SUMMARY OF THE INVENTION

These and other purposes and goals are achieved by the present invention which solves the disadvantages inherent in the prior art by providing a class of $^{10}B$-containing compounds useful for boron neutron capture therapy (BNCT) and a method of using $^{10}B$-containing compounds for BNCT. The class of compounds according to the present invention includes iodinated closo sulfidohydroborane monomers and dimers. In one embodiment, the monomeric compounds of the invention have the formula $B_mI_nH_{m-n-1}SH$, in which m is an integer between 5 and 12 and n is a positive integer less than m. In another embodiment, the dimers of these compounds have the formula $B_xI_yH_{x-y-2}S_2$, in which x is an integer between 10 and 24 and y is a positive integer less than or equal to x-2. Two of the preferred compounds of the invention are a periodinated monomeric sulfidohydrododecaborane (IBSH) (m=12, n=11) and a periodinated dimeric sulfidohydrododecaborane (IBSSB) (x=24, y=22). The dimeric compounds of the invention include two monomeric boranes linked through a disulfide bridge formed through the oxidation of sulfhydryl groups present on the monomers.

The compounds of the invention should contain at least a natural abundance of boron-10 isotope. Preferably, at least 95% of the boron atoms in the compounds are boron-10 atoms.

The iodine isotopes useful for the invention may be radioactive, preferably iodine-123 ($^{123}$I), but can also include $^{131}$I, or $^{125}$I. Alternatively, the iodine isotopes may be radiostable, preferably iodine-127 ($^{127}$I). The compounds of the invention may include radiostable and radioactive nuclides of iodine on a single borane molecule. The incorporated iodine isotopes permit imaging of the iodinated sulfidohydroboranes by an imaging technique such as computed tomography (CT) or single photon emission computed tomography (SPECT). The present invention also includes methods for preparing iodinated sulfidohydroboranes as therapeutic agents for use in BNCT.

The invention also includes a method of performing BNCT, which includes administering a boron compound of the invention to a patient; locating the patient's tumor by scanning the patient with a device capable of detecting the location and extent of boron uptake by the tumor; and directing a beam of thermal neutrons toward the tumor to permit neutron capture by the boron and the subsequent secondary irradiation of the tumor with the fission products of metastable $^{11}$B decay, i.e., alpha and $^{7}$Li particles.

For a better understanding of the present invention reference is made to the following description and tables, the scope of which is described in the claims.

DETAILED DESCRIPTION OF THE INVENTION

Figure 1:
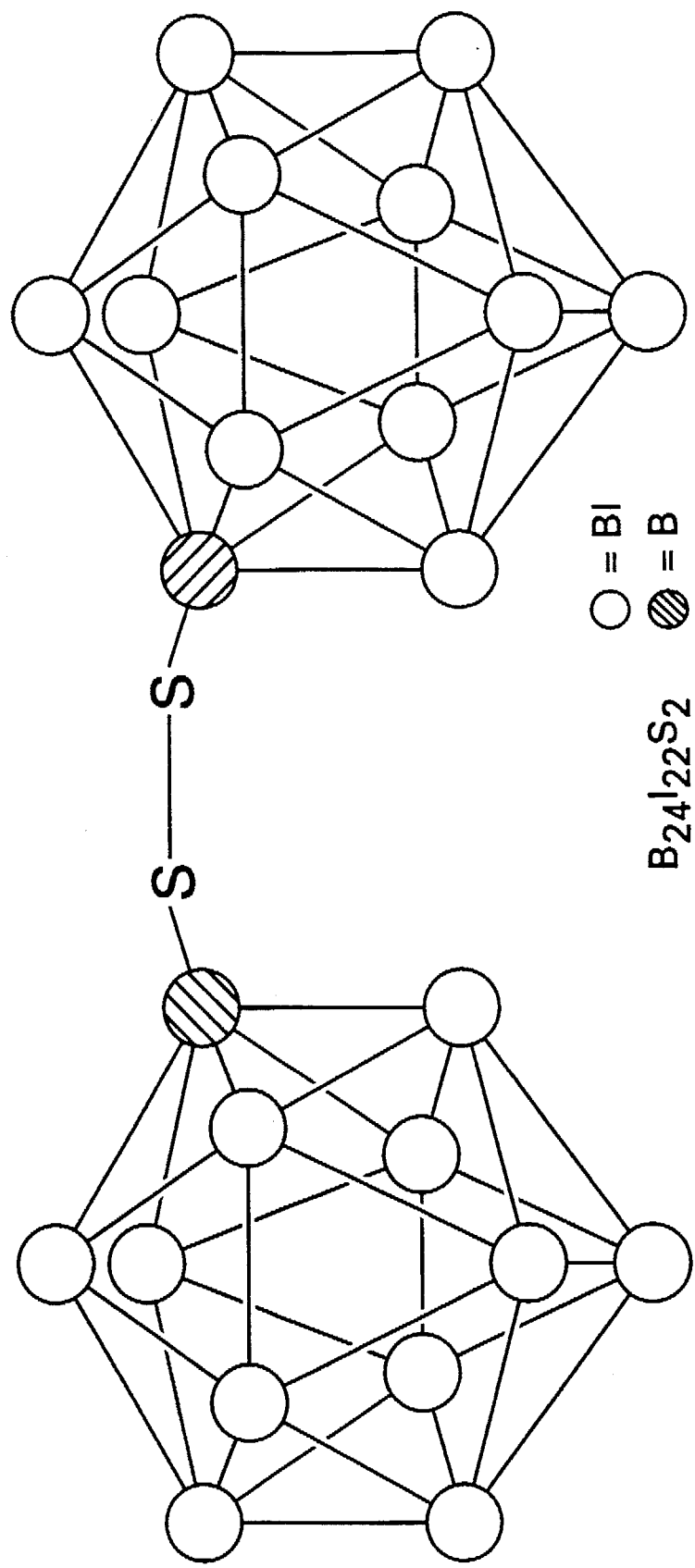
FIG. 1 illustrates the three-dimensional structure of a preferred dimeric compound of the invention.

A preferred embodiment of the present invention includes monomeric compounds having the formula $B_mI_nH_{m-n-1}SH$, in which m is an integer between 5 and 12 and n is a positive integer less than m. Another preferred embodiment includes the dimeric compounds having the formula $B_xI_yH_{x-y-2}S_2$, in which x is a positive integer between 10 and 24 and y is a positive integer less than or equal to x-2. The preferred compounds of the invention include a periodinated monomeric sulfidohydrododecaborane (IBSH) (m=12, n=11) and, more preferably, a periodinated dimeric sulfidohydrododecaborane (IBSSB) (x=24, y=22). The preferred dimeric compounds of the invention include two monomeric boranes linked through a disulfide bridge formed through the oxidation of sulfhydryl groups present on the monomers. The three-dimensional structure of a preferred dimeric compound of the invention is illustrated in FIG. 1.

The compounds of the invention should contain at least a natural abundance of boron-10 isotope. Preferably, at least 95% of the boron atoms in the compound are boron-10 atoms (i.e., 95 atom % boron-10).

The iodine isotopes useful for the invention may be radioactive, preferably iodine-123 ($^{123}$I), but may also include $^{131}$I, or $^{123}$I. Alternatively, the iodine isotopes may be radiostable, preferably iodine-127 ($^{127}$I). The compounds of the invention may include radiostable and radioactive nuclides of iodine on a single borane molecule. The incorporated iodine isotopes permit imaging of the iodinated sulfidohydroboranes by a technique such as CT or SPECT. The present invention also includes methods for preparing iodinated sulfidohydroboranes as therapeutic agents for use in BNCT.

The invention also includes a method of performing BNCT, which generally includes the following steps: administering a boron compound of the invention to a patient; locating the patient's tumor by scanning the patient with a device capable of detecting the location and extent of iodine and thereby, of boron uptake by the tumor; and irradiating the tumor with thermal neutrons to permit neutron capture by the boron and the subsequent secondary irradiation of the tumor with the fission products of metastable $^{11}$B decay.

Thus, the present invention provides an improved method of treating a patient having a malignant tumor using BNCT. In carrying out the method, a dose of a generally nontoxic or transiently toxic compound is administered in accordance with the present invention. The compound contains at least a natural abundance of, preferably at least about 95%, boron-10 that emits alpha and $^{7}$Li particles when bombarded with thermal neutrons. Preferably, the compound is administered to a patient parenterally, e.g., intraperitoneally or intravenously. The compound is administered in a dosage sufficient to permit the accumulation of the isotope in the tumor to a concentration of at least about 10. ppm, preferably at least about 30 ppm. A neutron source, emitting a beam of neutrons having an energy distribution effective for neutron capture, is directed toward the tumor. The patient is positioned so that the tumor is in the irradiation field of the neutron beam for a time sufficient to cause substantial inactivation of tumor cells and/or the cells of the tumor vasculature. One aspect of the present method includes using, as the compound of the present invention, a non-specific $^{10}$B-carrier, in particular, an iodinated sulfidohydroborane.

In several proposed BNCT methods, selective accumulation of boron compounds in specific tissues would be achieved by the use of antibody carriers for boron compounds. If the antibodies are monoclonal, these carriers are selected to specifically target a known antigen on a known tumor, which would limit their use to particular types of tumors.

One advantage of the borane monomers and dimers of the invention is that they are non-specific and therefore are generally useful for a variety of tumors, particularly brain tumors. The preferential accumulation of these boranes in brain tumors is believed to be due to a barrier to their diffusion from the normal brain tissue (i.e., the blood-brain-barrier). For example, gliomas are often associated with surrounding edematous brain tissue, likely the result of fluid leakage through leaky endothelial walls. Presumably, the leakage of boranes, reversibly bound to plasma proteins (mainly albumin), through the endothelial walls facilitates the diffusion of these compounds to the tumor environment. Meanwhile, these compounds are prevented from crossing the relatively impermeable endothelial barrier of non-edematous brain tissue. It has been observed that the dimeric borane BSSB is more readily accumulated in brain tumors than the monomeric form, see Slatkin et al., "Boron Uptake in Melanoma, Cerebrum and Blood from $Na_2B_{12}H_{11}SH$ and $Na_4B_{24}H_{22}S_2$ Administered to Mice", Biochem Pharm., 35, 1776 (1986). Accordingly, the dimeric iodinated borane IBSSB is likely to be preferable over the monomeric IBSH. The iodination of boranes, to produce the compounds of the invention, apparently does not result in serious interference with the tumor affinity of the boranes. This is a significant advantage over iodinated boron-containing antibodies, the affinity of which can be compromised by iodination.

As described above, the $^{10}B$ nucleus has a high probability of absorbing a nearby neutrons. The resulting metastable nucleus ($*^{11}B$) decays, emitting short range high LET alpha (i.e., $^4He$) and lithium-7 ($^7Li$) ionizing particles. Since the tissue penetration of these fragments is in the range of less than 10 micrometers, i.e., one-hundredth of one millimeter, the reaction is significantly destructive only to cells in the close vicinity of the decaying $^{11}B$ nuclei. The 480 keV gamma rays emitted by the $^{11}B$ decay are locally almost non-destructive to tissues and play an insignificant role in the therapeutic efficacy of BNCT. If the boron-containing compound is taken up selectively by a tumor, then the tissue ablation will be limited to the tumor site, to selectively destroy the cancer cells.

To accumulate the requisite amount of the iodinated borane compounds of the present invention in a tumor, generally a systemic dose of between about 10–50 mg $^{10}B$ per kg body weight in a pharmaceutically acceptable carrier is administered to a patient. The compound is administered in one or more doses, the last dose being given between about 1 hour and about one week prior to subjecting the patient to the neutron beam. The quantity of the borane compound used in any particular treatment depends on, among other circumstances, the boron-10 content of the compound and the toxicity of the compound. The timing of the neutron exposure depends upon the concentration in blood, which decreases rapidly with time than does the tumor concentration. In the event that the tumor-to-blood ratio is less than one, it can be increased by plasmapheresis, a clinically routine procedure. Multiple doses of the iodinated borane compounds of the present invention can be administered over a period of a few days prior to radiation treatment. The timing of the administration of the compound depends on various considerations that are well known to those skilled in the art of clinical BNCT, including the pharmacokinetic behavior of the compound, e.g., the rate of absorption of the compound into the tumor and into the tumor vasculature; and the rate of excretion and/or metabolism of the compound by the patient.

Methods have been proposed to noninvasively localize compounds for neutron-capture therapy, see Slatkin, "A History of Boron Neutron Capture Therapy of Brain Tumors", Brain, 114, 1609 (1991); Hainfeld, "Uranium-loaded Apoferritin with Antibodies Attached: Molecular Design for Uranium Neutron-Capture Therapy", Proc. Natl. Acad. Sci. USA, 89, 11064 (1992); Martin et el., "Induction of Double-Strand Breaks Following Neutron Capture by DNA-Bound Gd-157", Int. J. Rad. Biol. Phys. Chem. Med , 54, 205 (1987); Shih et al., "Gadolinium as a Neutron Capture Therapy Agent", Med. Phys., 19, 733 (1992). Nuclides such as $^{157}Gd$, $^{99m}Tc$, $^{111}In$ and $^{55}Mn$ generally form exchangable ionic rather than non-exchangable covalent bonds. It is desirable, however, to have an imaging nuclide bound covalently, and therefore stably, in vivo to a neutron-capture agent to assure correspondence between the localization of the imaging nuclide and the distribution of the capture agent. Because imaging nuclides such as isotopes of iodine (e.g., $^{123}I$ and $^{127}I$) form pharmacologically stable covalent bonds, an iodine-labeled $^{10}B$-carrier would enable the biodistribution of $^{10}B$ to be imaged noninvasively in patients to optimize and enable rapid quantification of neutron exposure for BNCT.

The calculated weight ratio of iodine to $^{10}B$ in IBSSB, a periodinated sulfidohydrododecaborane dimer of the invention, is about 11.5. As a result, the presence of this compound in a tumor, at a therapeutically adequate concentration of $^{10}B$, for example, 30 μg $^{10}B$ per gram tumor, will be associated with 345 μg I per gram tumor. This concentration is suitable for imaging a tumor in the brain and for quantifying the iodine in the image using CT without requiring a conventional contrast enhancement agent. Contrast enhancement in malignant gliomas is typically from about 1 to about 10 Hounsfield units (1 Hounsfield unit corresponds to 154 μg I/mL. tissue, and 1 Hounsfield unit = 2 EMI scale units, see Gado et al., "An Extravascular Component of Contrast Enhancement in Cranial Computed Tomography, "Radiology, 17, 589 (1975). It follows that each added Hounsfield scale contrast enhancement unit observed in tumor image pixel by CT after 95% $^{10}B$-enriched IBSSB administration would correspond to an additional 13.4 μg $^{10}B$/mL in the tumor zone corresponding to that pixel. Thus, the use of nonradioactive $^{10}B$-IBSSB as a combined radiographic contrast agent and $^{10}B$-carrier permits the use of $^{10}B$ concentrations effective for BNCT of malignant gliomas, while simultaneously permitting quantification by conventional CT.

Alternatively, the use of IBSSB in which the iodine is radioactive allows visualization and quantification of mere traces of iodine in the tumor by SPECT. Therefore, the mode of imaging used may vary depending on the isotope of iodine that is used. In practice, it may prove useful to combine radiostable and radioactive isotopes of iodine on the same IBSSB molecule. Similarly, a therapeutic composition having a mixture of the invented compounds, each possessing one or more stable or radioactive isotopes of iodine, is within the scope of the invention.

For BNCT research and preclinical studies, the microdistribution of boron delivered by $^{125}I$-labeled IBSSB is assessed using $^{125}I$-mediated silver-grain autoradiography in a contiguous photographic emulsion. A grain/disintegration efficiency approaching 50% is attainable, providing spatial resolution comparable to that feasible with tritium-based autoradiography. See Rogers, *Techniques of Autoradioqraphy*, Third Ed., Elsevier/North-Holland Biomedical Press, Amsterdam (1979).

The radiation beam clinically useful, for example, irradiating intracranial tumors according to the present invention, is a beam of epithermal neutrons, i e., neutrons possessing kinetic energies of between 0.4 eV and 10 keV. For example, the epithermal neutron source at the Medical Research Reactor at Brookhaven National Laboratory, in Upton, N.Y., has been found to produce sufficient quantities of neutrons having energies effective for BNCT in accordance with the invention. In particular, a beam from this source delivering a dose of 8 MW/min. has been found to be effective, as described by U.S. Pat. No. 5,144,026 to Gabel, incorporated by reference herein. In general, the beam must deliver neutrons which, at the tumor site, have an energy distribution sufficient to permit neutron capture by the boron-10.

To take advantage of the neutron capture phenomenon and the associated secondary irradiation, the beam cross-section is preferably larger than the diameter of the tumor being irradiated. Given the usual >3 cm diameter of brain tumors, the beam is most preferably on the order of about 5–10 cm in diameter. The patient is positioned in front of the neutron beam port so that the tumor is within the neutron irradiation field. The physical qualities of the beam and the boron distribution in and around the target tissue ensure that the radiation exposure of healthy tissue is minimized, while the exposure of tumor tissue is maximized.

EXAMPLE 1

In one method, compounds of the present invention have been synthesized by treatment of $B_{24}H_{22}S_2^{4-}$ (either the sodium or potassium form) with an appropriate quantity of iodine and iodine monochloride in suitable solvents such as methanol/water or a chlorinated hydrocarbon such as 1,1,2,2-tetrachloroethane. The synthesis of the periododisulfide is shown in Scheme I.

SCHEME I

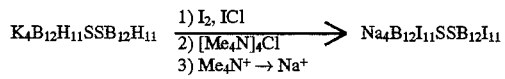

$Cs_4B_{12}H_{11}SSB_{12}H_{11}$ (100 mg, 0.114 mmol) (obtained from Callery Chemical Co., Callery, Pa.) was ion-exchanged to the $K^+$ salt (~57 mg). This was allowed to stir in a round-bottomed flask with $I_2$ (124 mg, 0.49 mmol) in 1,1,2,2-tetrachloroethane (4 mL) at room temperature for 15 min. under nitrogen. 1.0M ICl in dichloromethane (3.6 mL, 3.6 mmol) was added and allowed to stir at room temperature for 2 hrs. The solution was then heated to reflux for 32 hrs. After cooling, the solution was filtered. The solid was collected and dssolved in 1N NaOH until the dark red-brown color turned yellow or was slightly basic. The solution was filtered and to the filtrate was added $Me_4NCl$ (~0.10 g in 5 mL. water) which caused precipitation of the dimer. The product was collected and purified by recrystallization in 24% molar yield from BSSB. The beige-colored product was characterized by elemental analyses (Galbraith Laboratories Inc., Knoxville, Tenn.) and infrared (IR) spectroscopy, and shown to be most likely the tetramethylammonium salt of the periododimer $(Me_4N)_4I_{11}B_{12}SSB_{12}I_{11}$ [$(Me_4N)_4$IBSSB]. No BSSB was identified in the recrystallized product by thin layer chromatography.

The infrared spectrum of IBSSB showed a marked reduction in intensity of the strong absorbance at about $2500 \text{ cm}^{-1}$ (corresponding to BH stretching) from that of BSSB. This could be due to a minor contamination by BSSB or to incomplete iodination. Two absorbances appeared at 968 and $944 \text{ cm}^{-1}$ in IBSSB which were not present in the spectrum of BSSB. These correlate with BI stretching frequencies in $B_{12}I_{12}^{-2}$ (940 and 925 $\text{cm}^{-1}$), see Knoth, et. al, "Chemistry of Boranes. IX. Halogenation of $B_{10}H_{10}^{-2}$ and $B_{12}H_{12}^{-2}$", Inorg. Chem. 3, 159 (1964). The mercapto monomer can be obtained from the dimer using a reducing agent such as dithiothreitol and the cation can be exchanged to sodium with ion exchange chromatography.

EXAMPLE 2

An alternative method for the synthesis of these compounds according to the present invention, shown in Scheme II, is carried out by iodination of the hydroborane, $B_{12}H_{12}^{2-}$, followed by sulfurization of the iodohydroborane with N-methyl-benzothiazole-2-thione ("S" in Scheme II), for example, according to the method of Tolpin et al., "Synthesis and Chemistry of Mercaptoundecahydro-closo-dodecaborate(2–)", Inorg. Chem., 17, 867–2873 (1978). The iodo dimer (IBSSB) is synthesized from the resulting iodo monomer (IBSH) by oxidation.

SCHEME II

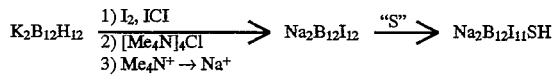

Periodination of $B_{12}H_{12}^{-2}$ is carried out under reaction conditions similar to those used for BSSB, see, for example, the method described by Knoth, et al., "Chemistry of Boranes. IX. Halogenation of $B_{10}H_{10}^{-2}$ and $B_{12}H_{12}^{-2}$", Inorg. Chem., 3, 159 (1964).

EXAMPLE 3

Iodine (0.20 mol) in methanol (400 mL) is added to a solution of $B_{12}H_{11}SSB_{12}H_{11}$ (0.10 mol) in 3:1 methanol:water (200 mL). The solution is neutralized with ammonium hydroxide and excess aqueous tetramethylammonium chloride is added. The resulting white precipitate is recrystallized from water. See Knoth et. al., "Chemistry of Boranes. IX. Halogenation of $B_{10}H_{10}^{-2}$ and $B_{12}H_{12}^{-2}$", Inorg. Chem., 3, 159 (1964).

EXAMPLE 4

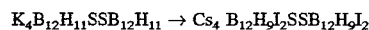

The same procedure is used for tetraiodination as with the diiodination (Example 3) except that two equivalents of iodine are used instead of one, e.g., 0.40 mol iodine.

EXAMPLE 5

The tetramethylammonium salt of the periodinated dimer described in Example 1 was ion exchanged to the sodium salt for a toxicity study in mice. Three groups of female mice (BNL Hale-Stoner strain) were given a single intraperitoneal (i.p.) injection of:

A) 17 µg B per gram of body weight (gbw) as $Na_4BSSB$ (6 mice),

B) 50 µg B/gbw as $Na_4IBSSB$ (4 mice), or

C) 0.9% NaCl in water (saline) (7 mice).

Injection volumes were all 0.015 mL/gbw. Five days after the injection, mice were euthanized by deep halothane inhalation anesthesia. Thoracotomy was performed, and about 0.7–0.9 mL blood was removed through the right ventricle. Hematological and chemical analyses were performed on blood specimens from each mouse.

Hematologic analyses were performed on the blood of mice given BSSB (Group A), IBSSB (Group B) or saline (Group C) in doses described above. The results of these analyses are shown in Table 1. The following abbreviations are used in Table 1: mouse group and number [MS], leukocytes [WBC] ($10^3$/µL), erythrocytes [RBC] ($10^6$/µL), hemoglobin [HGB] (g/dL), hematocrit [HCT] (%), mean erythrocyte volume [MCV] (µm$^3$), mean erythrocyte hemoglobin [MCH] (pg), mean erythrocyte hemoglobin concentration [MCHC] (100•MCH/MCV%), erythrocyte volume distribution width [RDW] (100•σ/MCV%), platelets [PLT] ($10^3$/µL), mean platelet volume [MPV] (µm$^3$), granulocytes [GRN] ($10^3$/µL), lymphocytes [LYM] ($10^3$/µL), and midrange-size locytes [MID] ($10^3$/µL).

TABLE 1

Hematologic analyses of the blood of mice given BSSB (Group A), IBSSB (Group B) or saline (Group C)

| MOUSE | WBC | RBC | HGB | HCT | MCV | MCH | MCHC | RDW | PLT | MPV | GRN | LYM | MID |
|---|---|---|---|---|---|---|---|---|---|---|---|---|---|
| A1 | 3.4 | 7.76 | 14.8 | 42.2 | 54.4 | 19.1 | 35.0 | 24.8 | 1090 | 4.80 | 0.10 | 3.2 | 0.10 |
| A2 | 5.1 | 8.81 | 7.1 | 49.2 | 55.8 | 19.4 | 34.8 | 24.9 | 1382 | 4.80 | 0.40 | 4.2 | 0.50 |
| A3 | 4.0 | 7.74 | 15.5 | 44.1 | 57.0 | 20.0 | 35.1 | 23.9 | 1101 | 4.90 | 0.30 | 3.4 | 0.30 |
| A4 | 4.9 | 8.81 | 17.0 | 47.9 | 54.4 | 19.3 | 35.5 | 23.7 | 1391 | 4.80 | 0.30 | 4.5 | 0.10 |
| A5 | 5.6 | 8.46 | 16.7 | 47.7 | 56.4 | 19.7 | 35.0 | 24.2 | 1316 | 4.50 | 0.70 | 3.9 | 1.0 |
| B1 | 2.6 | 8.05 | 15.6 | 44.8 | 55.6 | 19.4 | 34.8 | 24.2 | 1405 | 4.70 | 0.20 | 2.2 | 0.20 |
| B2 | 4.8 | 8.28 | 15.2 | 45.7 | 55.2 | 18.4 | 33.3 | 23.6 | 1395 | 5.10 | 0.20 | 4.5 | 0.10 |
| B3 | 4.4 | 7.92 | 15.5 | 43.4 | 54.8 | 19.6 | 35.7 | 23.9 | 1536 | 4.80 | 0.20 | 4.0 | 0.20 |
| C1 | 4.7 | 7.88 | 15.6 | 44.5 | 56.5 | 19.8 | 35.1 | 23.9 | 1384 | 4.50 | 0.30 | 4.2 | 0.20 |
| C2 | 4.4 | 8.72 | 17.5 | 48.7 | 55.9 | 20.1 | 35.9 | 23.8 | 1223 | 4.80 | 0.20 | 3.9 | 0.30 |
| C3 | 3.7 | 8.66 | 16.9 | 48.2 | 55.7 | 19.5 | 35.1 | 24.3 | 1334 | 5.00 | 0.50 | 2.6 | 0.60 |
| C4 | 3.3 | 8.64 | 16.7 | 48.3 | 55.9 | 19.3 | 34.6 | 24.5 | 1249 | 4.80 | 0.30 | 2.8 | 0.20 |
| C5 | 4.4 | 8.85 | 17.4 | 50.1 | 56.6 | 19.7 | 34.7 | 23.9 | 1222 | 4.80 | 0.40 | 3.6 | 0.40 |

Chemical analyses were performed on blood plasma from mice given BSSB (Group A), IBSSB (Group B) or saline (Group C) in doses described above, the results of which are shown in Table 2. The following abbreviations are used in Table 2: mouse group and number [MS], glucose [GLU] (mg/dL), blood urea nitrogen [BUN] (mg/dL), blood creatinine [BCR] (mg/dL) aspartate transaminase [AST] (U/L), alanine transaminase [ALT] (U/L), alkaline phosphatase [ALP] (U/L), creatine phosphokinase [CPK] (U/L), total protein [TPR] (g/dL), albumin [ALB] (g/dL), calcium [CA] (mg/dL), chloride [CHL] (meg/L), inorganic phosphorus [P] (mg/dL), potassium [K] (meg/L), and sodium [SOD] (meg/L).

compound, BSSB, which is known to be non-lethal at about 35 μg B/gbw, i.e., twice the lower of the two boron doses used See Slatkin et al., "Boron Uptake in Melanoma, Cerebrum and Blood from $Na_2B_{12}H_{11}SH$ and $Na_4B_{24}H_{22}S_2$ Administered to Mice", Biochem. Pharm., 35, 1771 (1986).

The fourteen chemical and thirteen hematological tests of blood from mice given either BSSB (Group A) or IBSSB (Group B) showed no significant differences between the two groups using the Wilcoxon Two-Sample test. See Miura et al., "Biodistribution and Toxicity of 2,4-Divinyl-nido-carboranyldeuterophorphyrin IX in Mice". Biochem. Pharm., 43, 467 (1992). It therefore appears that the periodinated borane is not more toxic than the non-iodinated borane.

TABLE 2

Chemical analyses of the blood plasma from mice given BSSB (Group A), IBSSB (Group B) or saline (Group C).

| MOUSE | GLU | BUN | BCR | AST | ALT | ALP | CPK | TPR | ALB | CA | CHL | P | K | SOD |
|---|---|---|---|---|---|---|---|---|---|---|---|---|---|---|
| A1 | 311 | 16 | 0.4 | 46 | 28 | 128 | 50 | 5.7 | 3.4 | 11.7 | 119 | 11.7 | 10.0 | 156 |
| A2 | 217 | 26 | 0.4 | 41 | 21 | 115 | 37 | 5.3 | 3.3 | 10.9 | 118 | 8.8 | 6.9 | 154 |
| A3 | 315 | 23 | 0.4 | 56 | 36 | 130 | 64 | 6.0 | 3.6 | 11.1 | 117 | 9.6 | 9.2 | 154 |
| A4 | 268 | 23 | 0.5 | 70 | 34 | 103 | 141 | 5.3 | 3.2 | 11.3 | 119 | 10.9 | 9.9 | 153 |
| A5 | 249 | 23 | 0.6 | 80 | 28 | 132 | 215 | 6.0 | 3.6 | 11.6 | 121 | 9.0 | 6.5 | 161 |
| A6 | 269 | 30 | 0.5 | 40 | 19 | 143 | 58 | 5.8 | 3.4 | 11.0 | 120 | 9.4 | 7.2 | 158 |
| B1 | 332 | 15 | 0.4 | 80 | 33 | 108 | 89 | 5.5 | 3.0 | 11.2 | 119 | 10.1 | 7.9 | 155 |
| B2 | 206 | 27 | 0.4 | 77 | 47 | 123 | 148 | 5.8 | 3.3 | 11.9 | 119 | 10.8 | 7.8 | 156 |
| B3 | 252 | 26 | 0.4 | 89 | 66 | 123 | 75 | 5.8 | 3.2 | 11.3 | 117 | 9.8 | 6.0 | 155 |
| B4* | 278 | 28 | 0.5 | 44 | 22 | 110 | 35 | 5.9 | 3.3 | 11.5 | 116 | 9.9 | 7.1 | 154 |
| C1 | 307 | 24 | 0.5 | 63 | 26 | 149 | 134 | 5.6 | 3.0 | 11.6 | 121 | 11.7 | 11.3 | 153 |
| C2 | 298 | 17 | 0.4 | 58 | 26 | 156 | 113 | 5.3 | 3.2 | 11.1 | 121 | 11.0 | 11.0 | 154 |
| C3 | 286 | 31 | 0.5 | 49 | 26 | 120 | 36 | 5.5 | 3.2 | 11.3 | 115 | 8.8 | 6.3 | 154 |
| C4 | 295 | 28 | 0.5 | 41 | 28 | 112 | 35 | 5.5 | 3.3 | 11.1 | 119 | 9.0 | 6.6 | 155 |
| C5** | 234 | 32 | 0.5 | 112 | 54 | 126 | 245 | 5.9 | 3.5 | 11.4 | 123 | 9.7 | 9.5 | 158 |
| C6 | 226 | 33 | 0.5 | 50 | 19 | 136 | 99 | 6.1 | 3.6 | 11.6 | 121 | 10.1 | 7.9 | 159 |
| C7 | 410 | 29 | 0.6 | 30 | 10 | 164 | 58 | 5.8 | 3.3 | 12.0 | 121 | 11.2 | 10.5 | 157 |

*Mouse not given entire dose of IBSSB; excluded from analyses.
**Mouse appears to have had liver dysfunction by its abnormal liver enzyme values; excluded from analyses.

As shown in Tables 1 and 2, a single i.p. injection of IBSSB at a dose corresponding to 50 μg B/gbw appears to have been only minimally more toxic than a similar injection of three-fold less BSSB, as Judged by hematological and chemical tests oft he blood 5 days later. Inadvertently, the BSSB group (Group A) received 17 μg $^{10}$B/gbw, only about one-third of the intended boron dose, 50 μg/gbw. Nevertheless, it is useful to compare the subacute toxicity of a relatively high dose of a substance, IBSSB, which had never before been tested in an animal, with that of its parent Alanine transaminase [ALT] levels in the mice given IBSSB (Group B) were significantly higher than those in mice given physiological saline (Group C). No other differences were noted between mice in groups B and C. We surmise from this preliminary in vivo experiment that IBSSB may be slightly hepatotoxic to mice, but there is no evidence of significant toxicity at blood concentrations believed to be useful for BNCT.

Thus while we have described what are presently the preferred embodiments of the present invention, other and further changes and modifications could be made without departing from the scope of the invention, and it is intended by the inventors to claim all such changes and modifications.

We claim:

1. A method of tumor radiotherapy, comprising the steps of:
   (a) administering to a patient having a tumor a radiotherapeutically effective amount of an iodinated sulfidohydroborane containing at least about 20 atom % boron-10 isotope;
   (b) locating said tumor by scanning the patient with a photoscanning device for detecting said iodine to determine the location and extent of selective accumulation of the iodinated sulfidohydroborane by the tumor; and
   (c) directing a beam of neutrons, having an energy distribution effective for neutron capture, at the tumor sufficient to produce neutron capture by said iodinated sulfidohydroborane in the immediate vicinity of the tumor for a duration sufficient to effect substantial tumor tissue and/or tumor vasculature deterioration.

2. The method of claim 1, further comprising selecting an iodine isotope from the group consisting of radiostable and radioactive isotopes of iodine.

3. The method of claim 1, further comprising selecting a boron-10 isotope content in said boron compound of at least about 95 atom %.

4. The method of claim 1, further comprising selecting as said iodinated sulfidohydroborane a compound having the formula

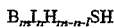
$$B_m I_n H_{m-n-1} SH$$

wherein m is an integer between 5 and 12, and n is a positive integer less than m.

5. The method of claim 4, further comprising selecting as said iodinated sulfidohydroborane a compound wherein m=12 and n=11.

6. The method of claim 4, further comprising selecting as said iodinated sulfidohydroborane a compound wherein m=12 and n=1.

7. The method of claim 4, further comprising selecting as said iodinated sulfidohydroborane a compound wherein m=12 and n=2.

8. The method of claim 1, further comprising selecting as said iodinated sulfidohydroborane a dimeric compound having the formula:

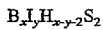
$$B_x I_y H_{x-y-2} S_2$$

wherein x is an integer between 10 and 24, and y is a positive integer less than or equal to x-2.

9. The method of claim 8, further comprising selecting as said dimeric iodinated sulfidohydroborane a compound wherein x=24 and y=22.

10. The method of claim 1, further comprising selecting as the iodinated sulfidohydroborane a compound from the group consisting of $B_{12}I_{11}SH^{-2}$, and $B_{12}I_{11}SSB_{12}I_{11}^{-4}$, and physiologically acceptable salts thereof.

11. The method of claim 1, wherein said administering step comprises parenterally administering said iodinated sulfidohydroborane.

12. The method of claim 1, wherein said administering step further comprises administering an amount of said iodinated sulfidohydroborane sufficient to selectively accumulate said boron-10 isotope in the tumor in a concentration of at least 10 ppm.

13. The method of claim 1, wherein said administering step further comprises administering an amount of said iodinated sulfidohydroborane sufficient to selectively accumulate said boron-10 isotope in the tumor in a concentration of at least 30 ppm.

14. An improved method of boron neutron capture therapy, including the steps of:
   (a) administering to a patient having a tumor a dose of a boron compound which contains at least about 20 atom % boron-10 that emits alpha and $^7Li$ particles when bombarded with neutrons, said compound being administered in a dosage sufficient to selectively accumulate said boron-10 in the tumor in a concentration of at least 10 ppm;
   (b) providing a source that emits neutrons having an energy distribution effective for neutron capture, said source having a port through which a beam of neutrons is emitted; and
   (c) positioning the patient so that said tumor is in the path of said beam for a time sufficient to effect substantial tumor tissue deterioration;

wherein the improvement comprises:
   adminstering as said boron compound an iodinated sulfidohydroborane.

15. The method of claim 14, further comprising administering as said sulfidohydroborane a compound selected from the group consisting of $B_{12}I_{11}SH^{-2}$, $B_{12}I_{11}SSB_{12}I_{11}^{-4}$, and physiologically acceptable salts thereof.

16. The method of claim 14, further comprising administering as said iodinated sulfiodohydroborane an iodinated sulfidohydroborane having a boron-10 content of at least about 95 atom %.

17. The method of claim 14, further comprising administering said boron compound in an dosage sufficient to selectively accumulate said boron-10 in the tumor in a concentration of at least 30 ppm.

* * * * *